United States Patent [19]

Fiato et al.

[11] Patent Number: 4,618,597

[45] Date of Patent: Oct. 21, 1986

[54] HIGH SURFACE AREA DUAL PROMOTED IRON/MANAGANESE SPINEL COMPOSITIONS

[75] Inventors: Rocco A. Fiato, Scotch Plains; Stuart L. Soled, Pittstown, both of N.J.

[73] Assignee: Exxon Research and Engineering Company, Florham Park, N.J.

[21] Appl. No.: 814,040

[22] Filed: Dec. 27, 1985

Related U.S. Application Data

[63] Continuation-in-part of Ser. No. 564,465, Dec. 20, 1983.

[51] Int. Cl.$^4$ .......................... B01J 23/02; B01J 23/34
[52] U.S. Cl. ..................................... 502/324; 502/325; 502/328; 502/330; 502/331; 502/338; 502/340; 502/344; 502/345; 502/524; 423/594; 423/599
[58] Field of Search .............. 502/241, 243, 250, 252, 502/258, 331, 304, 324, 325, 328, 330, 332, 344, 340, 350, 345, 318, 524; 423/594, 599

[56] References Cited

U.S. PATENT DOCUMENTS

| | | | |
|---|---|---|---|
| 2,605,275 | 7/1952 | Kearby et al. | 502/343 |
| 2,778,845 | 1/1957 | McGrath et al. | 502/324 |
| 2,846,488 | 8/1958 | Miller | 585/270 |
| 3,970,738 | 7/1976 | Matsui et al. | 423/140 |
| 4,152,300 | 5/1979 | Riesser | 502/324 |
| 4,177,203 | 12/1979 | Kobel et al. | 260/449.6 R |
| 4,186,112 | 1/1980 | Volgt et al. | 502/183 |
| 4,233,186 | 11/1980 | Duprez et al. | 502/324 |
| 4,239,658 | 12/1980 | Mitchell, III et al. | 502/324 |
| 4,256,722 | 3/1981 | Carrier | 423/594 |
| 4,299,735 | 11/1981 | Mein et al. | 502/324 |
| 4,425,250 | 1/1984 | Hibst | 423/594 |
| 4,544,674 | 10/1985 | Fiato et al. | 502/524 |

OTHER PUBLICATIONS

"Iron-Manganese Oxide Catalyst for Fisher-Tropsch Synthesis Part 1: Structural and Textural Changes by Calcination, Reduction, Synthesis"—Applied Catalysis, vol. 5 (1983), pp. 151-170, by G. C. Malti et al.
"Effects of Manganese Oxide and Sulfate on Olefin Selectivity of Iron Catalysts in Fischer-Tropsch Reaction"—Applied Catalysis, vol. 2 (1982), pp. 273-288, by W. L. Van Dijk et al.
"Synthesis of Hydrocabons and Oxygen-Containing Compounds from Carbon Monoxide and Hydrogen over Iron-Copper Catalysts", Khimya I. Tekhnolociya, Topliv I. Masel, No. 6, pp. 5-10, Jun. 1965 (Russian).
"Make Olefins from Synthesis Gas", Hydrocarbon Processing (Nov. 1980), pp. 139-142, by V. Rao and R. Gormley.
"Unconventional Olefin Processes", Hydrocarbon Processing, (May 1983), pp. 88-96, by Y. C. Hu.
"Feedstock for Chemical Industry by Selective Fisher-Tropsch Synthesis", by H. Kobel et al., 1978, Society of Automotive Engineers, p. 482.
"Development of a New Type of Catalysts for the Selective Fisher-Tropsch Synthesis", 73rd AICHE Meeting, Paper #103D, by H. J. Lehman et al.

*Primary Examiner*—Andrew H. Metz
*Assistant Examiner*—Anthony McFarlane
*Attorney, Agent, or Firm*—Edward M. Corcoran; Richard E. Nanfeldt

[57] ABSTRACT

Slurried, high surface area, Cu and Group IA or IIA dual metal promoted Mn-Fe spinels which are fully reduced and carburized provide exceptionally high catalytic activity and selectivity in the conversion of-Co/H$_2$ to alpha-olefins, particularly when reduced and carbided in-situ. These copper and Group IA or IIA metal promoted iron-manganese catalysts maintain good activity and selectively under low pressure reaction conditions.

16 Claims, No Drawings

HIGH SURFACE AREA DUAL PROMOTED IRON/MANAGANESE SPINEL COMPOSITIONS

This application is a continuation-in-part of copending U.S. Ser. No. 564,465 filed on Dec. 20, 1983.

BACKGROUND OF THE INVENTION

1. Field of the Invention

This invention relates to new, dual promoted, high surface area, iron/manganese spinel compositions promoted with copper and with a Group IA or Group IIA metal, the preparation and use. More particularly, this invention relates to new, unsupported, single phase Fe-Mn spinel compositions dual promoted with copper and a Group IA or Group IIA metal, their preparation and use as catalysts in Fischer-Tropsch slurry processes for producing alpha olefins from mixtures of CO and $H_2$. These catalysts have a surface area greater than about 30 $M^2/g$ in which the atomic ratio of Fe to Mn is greater than 2:1.

2. Background of the Disclosure

Fischer-Tropsch processes have long been known to produce gaseous and liquid hydrocarbons containing $C_2$-$C_4$ olefins. Because of the importance of $C_2$-$C_4$ olefins, particularly as feedstocks for the chemical industry, modifications of the Fischer-Tropsch process are constantly being pursued toward the goals of maximizing $C_2$-$C_4$ olefin selectivity with the particular objective of maintaining high catalyst activity and stability under the reaction conditions. The main thrust of the efforts in this area has been in the area of catalyst formulation.

Coprecipitated and/or supported iron-based catalysts, including those containing manganese, are known for producing $C_2$-$C_3$ olefins. Examples of disclosures in the art directed to such iron-manganese catalysts and/or alloys include: W. L. vanDijk, et al., *Appl. Catal.*, 2, 273 (1982); Eur. Pat. Appl. 49888 to Ruhrchemie (1981); H. J. Lehman, 73rd AICHe Meeting Paper #103D; W. D. Deckwer, et al., *Chem. Ing. Tech.*, 53 (10), 818 (1981); V. Rao and R. Gormley, *Hydrocarbon Processing*, 139, November (1981); H. Kolbel and K. Tillmetz, U.S. Pat. No. 4,177,203 (1970); EPO Patent Publication No. 0,071,770; U.S. Pat. No. 2,605,275; U.S. Pat. No. 2,850,515; *Prepr. Div. Pet. Chem. Am. Chem. Soc.* (1978) 23(2) pp 513-20; *Intersoc. Energy Convers. Eng. Conf.* 1978, 13(1) pp 482-6; U.S. Pat. No. 4,186,112; EP No. 49,888; React. Kinet. Catal. Lett. 1982, 20(1-2) pp 175-80; U.S. Pat. No. 2,778,845; *Khim.* (1) *Tekhnol. Topliv i Masel* (Russ.) 10(6) 5-10 (1965); UK Patent Appln. No. 2,050,859 A; German Patent Appln. DT No. 2919-921; *Prace Ustavu Vyzkum Paliv* 8, p. 39-81 (1964) (Czech).

An iron-manganese spinel of the formula, $Fe_2MnO_4$, is reported as a catalyst component formed during Fischer-Tropsch synthesis in which a coprecipitated Fe/Mn oxide catalyst is initially employed in *Applied Catalysis* 5 (1983) pp. 151-170.

U.S. Pat. No. 2,778,845 to McGrath, et al. discloses a non-spinel type, low surface area, sintered catalyst composition containing reduced or metallic iron as a major component. These compositions are used to synthesize hydrocarbons from mixtures of hydrogen and and carbon monoxide and are formed via a high temperature fusion in an electric arc furnace. The sintered or fused composition must then be reduced, preferably in hydrogen, to form the metallic iron-containing catalyst. U.S. Pat. No. 2,605,275 to Kearby, et al. discloses forming hydrocarbons from mixtures of CO and $H_2$ employing low surface area, sintered, spinel type catalysts containing iron and a divalent metal of the general formula $Fe_2MeO_4$ wherein Me is the divalent metal. The molar ratio of Me to $Fe_2O_3$ is preferably greater than 1:1. Thus, the ratio of Fe/Me is no greater than 2/1 and preferably less than 2/1.

U.S. Pat. No. 3,970,738 to Matsui, et al. discloses an iron oxide composition containing a minor amount of manganese oxide and a process for making same. The object of the invention in this disclosure is stated as being able to provide iron oxide products substantially free from manganese compounds as impurities. The upper limit on the manganese component of these iron oxide products is taught and claimed as being less than 0.2 weight percent calculated as MnO. Maiti, et al. in "Iron/Manganese Oxide Catalysts for Fischer-Tropsch Synthesis. Part I: Structural and Textural Changes by Calcination, Reduction and Synthesis", J. Applied Catalysis, v5, p. 151-170 (1983) discloses the use of iron-manganese containing catalysts in a Fischer-Tropsch process to produce olefins. Spinel compositions are suggested as being present in the catalysts used in this reference. This reference does not disclose the use of copper and potassium promoted spinels.

Van Dijk, et al. in "Effects of Manganese Oxide and Sulfate on the Olefin Selectivity of Iron Catalysts in the Fischer Tropsch Reaction", J. Applied Catalysis, v2, p. 273-288 (1982) disclose a Fischer-Tropsch catalyst which, on page 277, is set forth as a mixture of alpha iron oxide, alpha iron hydroxide and $Mn_2O_3$. This reference discloses that these catalysts produce substantially more than about 20% methane make and an equilibrium methane selectivity (on page 283) of over 30%. U.S. Pat. No. 4,177,203 to Kolbel, et al. discloses, in line 6-9 of column 3, a Fischer-Tropsch process using a catalyst which contains more than 50% manganese and less than 50% iron. This process produces low molecular weight olefins. Kolbel, et al. in "Feedstock For Chemical Industry By Selective Fischer-Tropsch-Synthese", 1978 Society of Automotive Engineers, p. 482-486, disclose a Fischer-Tropsch catalyst consisting of a precipitated mixture of gamma $Mn_2O_3$ and alpha $Fe_2O_3$ inserted in the manganese oxide lattice. Thus, the catalyst composition of this reference consists of mixed oxide phases. Further, the ratio of manganese to iron oxide of the catalyst disclosed therein is set forth as being between 8 and 10.

Europan Pat. No. 71,770 discloses iron-manganese catalysts promoted with potassium, wherein the maximum ratio of iron to manganese is 1:2. Compositions set forth in the Tables on pages 11 and 13 of this reference disclose iron/manganese ratios of 1:3.

Bruce, et al. in "Light Olefin Production from $CO/H_2$ Over Silica Supported Fe/Mn/K Catalysts Derived From a Bimetallic Carbonyl Anion, [$Fe_2Mn(CO)_{12}$]", React. Kinet. Catal. Lett., v. 20, Nos. 1-2, p. 175-180 (1982) disclose olefin production using supported catalysts prepared from carbonyl precursors, with silica being the support. Methane selectivity incurred with the use of this catalyst in Fischer-Tropsch hydrocarbon synthesis reactions is disclosed as about 31% (unpromoted) and 18% (potassium promoted).

Jenson, et al. in "Studies on Iron-Manganese Oxide Carbon Monoxide Catalysts; I. Structure of Reduced Catalyst", J. of Catalysts, v. 92, p. 98-108 (1985) disclose iron-manganese catalysts showing enhanced selectivity for low molecular weight olefins from synthesis gas. The reduced catalyst composition is disclosed as having been found to be an alpha iron oxide and a manganese (II oxide) as separate phases, with the manganese oxide phase containing some divalent iron oxide in solid solution. Maiti, et al. in "Iron/Manganese Oxide Catalysts For Fischer-Tropsch Synthesis. Part II, Crystal Phase Composition, Activity and Selectivity" J. Appl. Catal. 16 (2) 215–25 (1985) disclose structural changes in the Fe-Mn oxide system under synthesis gases as a function of various pretreatments.

French Pat. No. 2,554,433 discloses passing a mixture of $H_2$ and CO over a spinel catalyst having the general formula of $Li_xCu_{1-x}Fe_5O_8$ and French Pat. No. 2,553,399 discloses a similar process employing a catalyst having the general formula of $Cu_xMn_{1-x}Fe_yCr_{1-y}O_4$.

Finally, Pennline, et al. in "The Effect of Activation and Promotion on a Fischer-Tropsch Catalyst" 189th ACS National Meeting (Miami Beach 4/28-5/3/85) ACS Div. Fuel Chem. Prep. 30# 3:310-17 (1985) disclose a Fischer-Tropsch catalyst employed in a slurry reactor employing catalysts containing 21% iron 79% manganese oxide activated in-situ, under various conditions.

However, none of the references cited above describe a Fisher-Tropsch hydrocarbon process employing an unsupported single phase Fe/Mn spinel catalyst having an Fe:Mn atomic ratio above 2:1 and a surface area greater than about 30 $M^2/g$ and being dual promoted with both copper and a Group IA or IIA metal promoter agent.

SUMMARY OF THE INVENTION

The present invention relates to relatively high surface area, unsupported, single phase, iron-manganese spinels which are dual promoted with both copper and a Group IA or IIA metal useful for synthesizing alpha olefins from mixtures of CO and $H_2$ in a slurry process, said spinels having the empirical formula:

$Fe_xMn_yO_4$ wherein x and y are integer or decimal values, other than zero, with the proviso that the sum of x+y is 3 and the ratio of x/y is above 2:1, wherein said spinel exhibits a powder X-ray diffraction pattern substantially isostructural with $Fe_3O_4$, with said promoter metals being substantially deposited on the surface of said spinel and said surface area of said spinel being greater than about 30 $M^2/g$.

These catalyst compositions provide greater catalytic activity and also greater selectivity towards alpha olefins than similar compositions such as the relatively low surface area iron-manganese spinels, not promoted with copper, which are disclosed in co-pending U.S. patent application Ser. Nos. 564,464 and 564,464 filed on Dec. 20, 1983. Further, the catalyst compositions of this invention are active both in fixed bed and in slurry hydrocarbon synthesis processes, compared to the catalysts of said co-pending applications which are substantially inactive in slurry processes.

The high surface area catalyst compositions of this invention can be prepared by a process of adding an alpha-hydroxy aliphatic carboxylic acid, e.g., glycolic acid, to an acidic aqueous solution containing dissolved iron and cobalt salts and subsequently evaporating the solution to dryness to yield an amorphous, mixed metal glycolate, which, on calcining at elevated temperature, forms a mixed metal oxide exhibiting a spinel crystal structure and possessing a high surface area. The unsupported, high surface area Mn-Fe spinels prepared in this manner possess BET surface areas greater than 30 $M^2/g$. Typically the spinels of this invention will have surface areas ranging between about 50–200 $M^2/g$.

The so-formed mixed metal oxide or spinel is then converted to the catalyst by contacting, at elevated temperature, with a mixture of $H_2$ and CO to form the reduced-carbided catalyst. Preferably the reduction and carbiding is accomplished in-situ in a slurry bed.

The spinels prepared according to the process of this invention may be promoted by surface impregnation or deposition with Group IA or Group IIA and copper metal salts prior to the reduction and carbiding step.

DETAILED DESCRIPTION OF THE INVENTION

The unsupported, high surface area, copper and alkali- or alkaline earth metal salt promoted iron-manganese single phase spinels of this invention are new compositions of matter which are isostructural with $Fe_3O_4$, as determined by X-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel, $MgAl_2O_4$, A and B can have the following cationic charge combinations: A=+2, B=30 3, A=+4, B=+2, or A=+6, B=30 1. Spinels contain an approximately cubic close-packed arrangement of oxygen atoms with ⅛th of the available tetrahedral interstices and ½ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp 1–30, (1964). By the term "isostructural" is meant crystallizing in the same general structure type such that the arrangement of the atoms remains very similar with only minor change in unit cell constants, bond energies and angles. By the term "single phase spinel", as used herein, is meant one structural and compositional formula, corresponding to a single spinel material into which all of the metal components are incorporated, and exhibiting one characteristic X-ray diffraction pattern.

The copper and Group IA or Group IIA metal promoted iron-manganese spinels of this invention possesses a BET surface area of over 30 $M^2/g$ and typically of from about 50–100 $M^2/g$ with about 100 $M^2/g$ being a general average surface area, as determined by the well-known BET surface area measurement technique as described in the reference JACS 60, p. 309 (1938) by S. Brunauer, P. H. Emmett, and G. Teller. This range of surface area generally corresponds to a particle size range of about 100 to 200 angstroms.

The spinel can be represented by the formula: $Fe_xMn_yO_4$, wherein x and y are decimal or integer values, other than zero, and wherein the sum of x plus y is 3, and the ratio of x to y is greater than 2:1, preferably being from above 2:1 to about 19:1. Particularly preferred is where the iron to manganese atomic ratio is about 3:1 to 7:1. The composition can further be comprised of a mixture of single phase spinels, of different iron-manganese atomic ratios.

Representative examples of the various spinels corresponding to the formula are $Fe_{2.85}Mn_{0.15}O_4$, $Fe_{2.625}Mn_{0.375}O_4$, $Fe_{2.25}Mn_{0.75}O_4$. A dual promoted spinel composition of the subject invention which is set forth in the Examples below is $Fe_{2.25}Mn_{0.75}O_4/2\%$ K, 1% Cu.

In general, the physical properties of the subject spinels of this invention are similar to those of magnetite and include melting point of above 1400° C., and a color of brownish-red. The dual promoted, iron-manganese spinels of this invention are used in unsupported for in $H_2/CO$ hydrocarbon synthesis.

Representative examples of suitable classes of the copper and Group IA and IIA metal promoter agents include carbonates, bicarbonates, organic acid and inorganic acid salts e.g. acetates, nitrates, halides, and hydroxide salts of copper and Group IA and IIA metals including lithium, sodium, potassium, cesium, rubidium, barium, strontium, magnesium and the like. The use of sulfate salts of the promoter metal should be avoided, because it has been found that the resulting catalyst will be inactive in the slurry process.

Representative examples of specific promoter agents include copper carbonate, copper bicarbonate, copper nitrate, potassium carbonate, potassium bicarbonate, cesium chloride, rubidium nitrate, lithium acetate, potassium hydroxide, and the like. Group IA compounds are preferred with the copper with potassium being particularly preferred. The Group IA and IIA promoters will be present in an amount of from about a 0.1 to 10 gram-atom % of the total gram-atoms of metals present. A preferred level of promoter agent is in the range of 1 to 2 gram-atom % of the total gram-atom metal present. In the empirical formulas used herein, the amount of the promoter agent, e.g., potassium, is expressed in terms of gram atom percent based on the total gram-atoms of metal used. Thus, "1 gram-atom percent of potassium signifies the presence of 1 gram-atom of potassium per 100 total gram atoms of combined gram atoms of Fe and Mn. Thus, the symbol "/1% K" as used herein indicates 1 gram-atom percent potassium based on each 100 gram atom of the total gram atom of iron and manganese present.

The copper promoter metal will be present in the catalyst in an amount of from about 0.1 to 2.0 gram-atom percent based on the total metal content of the final catalyst composition and preferably from about 0.5 to 1.5 gram-atom percent.

The utility of these spinels is their ability upon subsequent reduction-carbiding, preferably in-situ in a slurry bed, to form active catalysts useful for making $C_2$–$C_{20}$ olefins from CO/hydrogen in a Fischer-Tropsch slurry process.

The reduced-carbided forms of the above-described spinel are also subjects of this invention.

The copper and Group IA or IIA metal promoted spinels undergo unexpectedly facile in-situ reduction in a slurry liquid and pretreatment to form copper and Group IA or IIA metal promoted iron-manganese spinels in reduced form, which are further in-situ carbided to form slurry catalysts active in a Fischer-Tropsch slurry process for making $C_2$–$C_{20}$ olefins from CO/hydrogen.

The spinels can be made by a process in which an aqueous solution of manganese and iron salts of an alpha-hydroxy aliphatic carboxylic acid, is evaporated to dryness, leaving an amorphous residue, which is then heated at elevated temperature to substantially form the spinel, as a single spinel phase, being isostructural with $Fe_3O_4$ and possessing a surface area greater than 3 $M^2/g$, preferably above 50 $M^2/g$. The heating is conducted such that no significant loss in surface area of the final spinel is incurred.

The key to the synthesis of these high surface area spinels is in the use of an organic, saturated, aliphatic, alpha-hydroxy carboxylic acid to form a complex salt, which is soluble in the aforementioned aqueous medium, at a pH on the acidic side, i.e., pH of 5–7. The solubility of the iron and manganese organic salts of the alpha-hydroxy carboxylic acid prevent crystallization from occurring, which would result in a crystalline product being obtained from the solution, that would possess a relatively low surface area.

This method of preparation utilizes an alpha-hydroxy aliphatic carboxylic acid which acts as a solubilizing agent for the iron and cobalt salts in the aqueous solution. Any saturated aliphatic alpha-hydroxy carboxylic acid, containing at least one alpha-hydroxy grouping, can be used to form the soluble iron and manganese salts in the subject invention process in aqueous solution, is deemed to be included within the scope of this invention. Representative examples of such acids which can be mono-hydroxy or di-hydroxy or mono-carboxylic or di-carboxylic are glycolic, malic, glyceric, mandelic, tartaric, lactic acids and mixtures thereof. A preferred carboxylic acid used in the process is glycolic acid.

The amount of acid used is at least the stoichiometric amount, i.e., 1 to 1 molar ratio for each metal present and preferably in about a 5–10% molar excess of the stoichiometric amount. Higher ratios can be used, if it is economical to do so. Lower amounts can also be used but would result in incomplete iron and cobalt acid salt formation.

The first step in the process comprises forming an aqueous solution by dissolving iron salts and manganese salts, in a water-soluble salt form such as their nitrates, sulfates, chlorides, acetates, and the like, in water.

The concentration of the salts in the aqueous liquid is not critical to the extent that the salts are present in less than a saturated solution to avoid precipitation. For example, an 80–90% saturated solution, of combined dissolved metal molarities for avoiding precipitation in the process, can be effectively used.

The temperature of the aqueous solution is not critical and may be above room temperature to aid in the solubilizing process. However, room temperature is adequate and is the temperature generally used in the process. The pressure also is not critical in the process and atmospheric pressure is generally used.

The aqueous solution can also contain a small amount of organic solvent such as ethanol, acetone, and the like for aiding in the solubilizing of the iron and manganese salts of the alpha-hydroxy carboxylic acid.

Following the dissolving of the iron and manganese salts, the alpha-hydroxy carboxylic acid is added, together with a sufficient quantity of base, usually being ammonium hydroxide, sodium hydroxide, potassium hydroxide, and the like, preferably ammonium hydroxide, to solubilizing the resulting acid salts. The amount of base added is sufficient to keep the pH in the range of about 5 to 7.0.

It should be noted that the exact sequence of steps need not be adhered to as described above, with the proviso that the resulting aqueous solution contain dissolved iron and manganese salts in stoichiometric amounts as iron and manganese salts of alpha-hydroxy carboxylic acid in solution. If there are any insoluble materials present after addition of the base and organic acid, they should be filtered prior to the evaporation step.

At this point, the resulting solution is evaporated, as for example, by air drying, or under reduced pressure, at elevated temperature, as practiced in a rotary evaporator, or in a vacuum drying oven.

The resulting material from the evaporation step is an amorphous residue, generally being a powder. This residue is heated at elevated temperature at 100° to 350° C. preferably 100°-200° C. and still more preferably 150°-200° C. for about 1 to 24 hours in generally air to result in a substantially single spinel phase which is isostructural with $Fe_3O_4$, as determined by X-ray diffractometry, as previously described herein. Preferred temperature range is 100°-400° C., and particularly preferred is about 350° C. for single phase spinel formation.

The dual promoted spinel is then reduced and carbided to form the catalyst. This reduction and carbiding is done by contacting the dual promoted spinel, at elevated temperature, with a suitable reactant such as CO, $CO/H_2$, aliphatic or aromatic hydrocarbons, and the like. Preferably the reduction and carbiding is accomplished simultaneously with a mixture of $CO/H_2$ with a $CO/H_2$ molar ratio of from about 1:10 to 10:1. A ratio of 1:2 has been found to be convenient in the laboratory. Still more preferably this reduction and carbiding will be accomplished in-situ in a slurry liquid in a reactor.

The reduction-carbiding step is generally conducted at a temperature of about 250° C., or above and preferably at 300° to 400° C. and still more preferably 270°-290° C. A preferred method of reducing and carbiding the catalyst is in-situ in the slurry liquid to be used in the Fischer-Tropsch process. A particularly preferred method is where the promoted spinel is treated with a mixture of CO/hydrogen and reduced and carbided in-situ in one step prior to hydrocarbon synthesis. The pressure is generally about 1 atmosphere, and a space velocity of about 20-20,000 v/v/hr is chosen in order to completely carbide the iron present in the spinel.

The resulting carbide is an active slurry catalyst for producing $C_2-C_{20}$ olefins in the described Fischer-Tropsch slurry process.

Also, a subject of the instant invention is a Fischer-Tropsch process for producing $C_2-C_{20}$ olefins by utilizing the Group IA or IIA metal and copper promoted iron-manganese spinel, and the reduced, carbided, Group IA or IIA metal and copper promoted iron-manganese spinel catalyst described hereinabove.

Although a fixed bed process can be used, a preferred process mode for operating the Fischer-Tropsch process utilizing the catalysts described herein is a slurry-type process wherein the catalyst in fine particle size and high surface area being above 30 $M^2/g$ is suspended in a liquid hydrocarbon and the CO/hydrogen mixture forced through the catalyst slurry allowing good contact between the CO/hydrogen and the catalyst to initiate and maintain the hydrocarbon synthesis process.

Advantages of a slurry process over that of a fixed bed process are that there is better control of the exothermic heat produced in the Fischer-Tropsch process during the reaction and that better control over catalyst activity maintainance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products residence time in the reaction zone.

The slurry liquid used in the slurry process must be liquid at the reaction temperature, must be chemically inert under the reaction conditions and must be a relatively good solvent for CO/hydrogen and possess good slurrying and dispersing properties for the finely divided catalyst. Representative classes of organic liquid which can be utilized are high boiling paraffins, aromatic hydrocarbons, ethers, amines, or mixtures thereof. The high boiling paraffins include $C_{10}-C_{50}$ linear or branched paraffinic hydrocarbons; the aromatic hydrocarbons include $C_2-C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. The slurry liquid can contain N and O in the molecular structure but not S, P, As or Sb, since these are poisons in the slurry process. Representative examples of specific liquid slurry solvents useful are dodecane, tetradecane, hexadecane, octadecane, cosane, tetracosane, octacosane, dotriacontane, hexatriacontane, tetracontane, tetratetracontane, toluene, o-, m-, and p-xylene, mesitylene, $C_1-C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvent is octacosane or hexadecane.

The amount of catalyst used in the liquid hydrocarbon slurry solvent is generally about 1 to 100 g. of dry catalyst per 500 g. slurry liquid. Preferably about 5 to 50 g. dry catalyst per 500 g. slurry liquid slurry is utilized, being in about a respective 5:1 to 100:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases.

In the process, the hydrogen and CO are used in a molar ratio in the gaseous feedstream in about a 10:1 to 1:10 molar ratio, preferably 3:1 to 0.5:1, and particularly preferred 1:1 to 2:1 molar ratio.

The temperature used in the process of this invention will generally be at least about 250° C., i.e., 250°-300° C., preferably being 260° to 280° C., and particularly preferred 240°-270° C. Higher temperature ranges can also be used but tend to lead to lighter products and more methane, lower temperature ranges can also be used but tend to lead to lower activity and wax formation. The pressure useful in the process of this invention will range between about 50 to 400 psig and preferably about 70 to 225 psig. Higher pressures can also be used but tend to lead to waxy materials, particularly in combination with lower temperature.

The space velocity used in the process is generally about 100 to 20,000 volumes of gaseous feedstream/per volume of dry catalyst in the slurry/per hour and is preferably in the range of about 1,000 to 15,000 v/v/hr, more preferably 1,000–10,000 v/v/hr and still more preferably 5,000 to 10,000. Higher space velocities can also be used but tend to lead to lower % CO conversion, and lower space velocities can also be used but tend to lead to more paraffinic products.

The percent CO conversion obtainable in the subject process, while providing substantial quantities of $C_2$–$C_{20}$ olefins, ranges from about 30 to 80 percent and usually about 50 to 60 percent for sufficient $C_2$–$C_{20}$ olefin production.

"Total hydrocarbons" produced in the process is related to the selectivity of percent CO conversion to hydrocarbons being those hydrocarbons from $C_1$ to about $C_{40}$ inclusive. Total hydrocarbon selectivity is generally 0 to 70 percent and higher, of the total CO converted, and the remainder converted to $CO_2$.

The percent $C_2$–$C_{20}$ hydrocarbons of the total hydrocarbons produced including methane and above is about 60 to 90 wt. %. The percent of $C_2$–$C_{20}$ olefins produced, of the $C_2$–$C_{20}$ total hydrocarbons produced is about 60 to 70 wt. %. The olefins produced in the process are substantially alpha olefins.

The selectivity to methane based on the amount of CO conversion is about 1 to 10 weight percent of total hydrocarbons, produced. Preferably about 5 percent, and lower, methane is produced in the process.

As discussed above, the percent selectivity to $CO_2$ formation in the process is about 10 to 50 percent of CO converted.

Preferably, the reaction process variables are adjusted to minimize $CO_2$ production, minimize methane production, maximize percent CO conversion, and maximize percent $C_2$–$C_{20}$ olefin selectivity, while achieving activity maintenance in the catalyst system. In the laboratory, it is convenient to use octacosane as the slurry liquid employing a catalyst represented by the formula $Fe_{2.25}Mn_{0.75}O_4$/1% Cu, 2% K and the catalyst/liquid weight ratio of 7/500, while stirring the slurry at 600 rpm. The conditions used in the laboratory both to activate the catalyst in-situ in the slurry liquid and to conduct the Fischer-Tropsch hydrocarbon synthesis process include an $H_2$/CO molar ratio of 2:1, a temperature of about 270° C., a total pressure of 75 psig and space velocity of 1,000–12,000 v/v/hr. These conditions have been found to result in efficient maintenance of the catalyst activity and $C_2$–$C_{20}$ olefin production.

The effluent gases in the process exiting from the reactor may be recycled if desired to the reactor for further CO hydrocarbon synthesis.

Methods for collecting the products in the process are known in the art and include fractional distillation, and the like. Methods for analyzing the product liquid hydrocarbons and gaseous streams are also known in the art and generally include gas chromatography, liquid chromatography, high pressure liquid chromatography and the like.

This invention will be more readily understood by reference to the examples below.

EXAMPLES

Unless otherwise indicated, the selectivity weight percentages, based on carbon, of product hydrocarbons is given on a $CO_2$-free basis.

Catalyst Evaluation Under CSTR-Slurry Reactor Conditions

Into a slurry reactor, being a 300 cc Parr CSTR (continuous stirred tank reactor) was charged: 72 g of octacosane and 0.5–8.0 g. of the spinel or catalyst being studied. The system was purged with nitrogen while the temperature was increased from room temperature to 200° C. The system was then placed under CO hydrogenation reaction conditions by adjusting the reaction temperature to 270° C., the $H_2$/CO volume ratio to 2:1, the space velocity to 1500–24,000 V gaseous feedstream/V dry catalyst/hr, the pressure to 75 psig, and the slurry stirrer speed to 600 rpm in the octacosane solvent. The effluent gas from the reactor was monitored by an HP-5840A Refinery Gas Analyzer to determine percent CO conversion and the nature of the hydrocarbon products.

EXAMPLE 1

Preparation and Evaluation of High Surface Area $Fe_{2.25}Mn_{0.75}O_4$ Spinel 39.1 grams of ferric nitrate ($Fe(NO_3)_3.9H_2O$) in 55 cc of water and 9.3 grams of manganese nitrate $Mn(NO_3)_2.6H_2O$ in 10 cc of water were mixed together. A solution was prepared by adding to 11.5 grams of 85% glycolic acid a sufficient amount of ammonium hydroxide such that the resulting pH of the ammonium glycolate solution was about 6.5. The ammonium glycolate solution consituted 0.129 moles of glycolic acid such that about a one to one molar ratio of iron and manganese metal to glycolic acid resulted. The ammonium glycolate solution was added to the aqueous solution containing iron and manganese salts and the contents stirred. The resulting solution was allowed to evaporate by air drying at room temperature.

The resulting dry solid was shown by X-ray diffraction to be an amorphous material because of lack of sharp, discrete reflections. The solid was heated in air at 175° C. for two hours. An X-ray diffraction pattern of the resulting material showed it to be a single phase, manganese/iron spinel isomorphous with $Fe_3O_4$. The X-ray diffraction peaks were broadened relative to a compositionally equivalent material obtained by a higher temperature procedure. This indicated that the resulting obtained material was of very small particle size. The surface area of the resulting material was about 100 square meters per gram.

The resulting material was then impregnated with (one or two) gram atomic percent of potassium using an aqueous solution of potassium carbonate and drying the resulting impregnated sample at 125° C. The resulting solid had an empirical formula of $Fe_{2.25}Mn_{0.75}O_4$/2%K. For the samples also containing the Cu promoter, 1 gm atom % of Cu, via an aqueous copper nitrate solution was impregnated onto the sample which was then dried at 125° C.

EFFECT OF CATALYST LOADING

A number of runs were made in the CSTR reactor with each run employing a different amount of catalyst which varied from 1 to 8 grams. The results are set forth in Table 1 below.

TABLE 1

CSTR PERFORMANCE OF $Fe_{2.25}Mn_{0.75}O_4$/2% K, 1% Cu

| GMS Catalyst | 1 | 2 | 4 | 8 |
|---|---|---|---|---|
| % CO Conversion | 68.9 | 83.0 | 87.0 | 87.0 |
| Wt % Selectivity (based on $C_1$+ hydrocarbons) | | | | |
| $CH_4$ | 1.7 | 2.3 | 2.8 | 4.1 |
| % α-olefin in $C_2$-$C_4$ | 93.5 | 92.0 | 93.0 | 92.0 |
| % α-olefin in $C_{10}$ | 63.1 | 64.7 | 65.0 | 55.0 |

Conditions: 270° C., 75 psi, $H_2$:CO:$N_2$ SCCM = 120:60:20, 72 gm octacosane solvent, 30+ hr on feed.

The data in Table 1 above show the high α-olefin selectivity obtained with the catalyst of this invention when operated under slurry reaction conditions with less than 10% wt. catalyst loading. Due to its high intrinsic activity, this catalyst is able to convert large quantities of $H_2$/CO feed even at the relatively low catalyst loadings employed.

EXAMPLE 2

Effect of Promoter and Surface Area

The $Fe_{2.25}Mn_{0.75}O_4$ high surface area spinels were prepared following the procedure in Example 1.

For comparison purposes, low surface area (BET 0.21 $M^2$/g) catalysts (Runs 4 and 5) were prepared according to the procedure set forth in Example 1 of copending U.S. application Ser. No. 564,464. Thus 17.293 g. of $Fe_2O_3$, 1.5119 g. Fe and 6.1946 g. of $Mn_3O_4$ were carefully weighed, thoroughly mixed and placed into a quartz tube (15 mm i.d., 18 mm o.d.) evacuated to $10^{-3}$ torr, sealed under vacuum and then heated to 800° C. for 24 hours. The resulting solids were isolated, thoroughly reground, pelletized and resubjected to the same high temperature sintering process at 800°-1000° C. for an additional 24 to 48 hours. Powder X-ray diffraction analysis was then conducted to ensure that the material was single phase and isostructural with $Fe_3O_4$. The catalyst pellets were then impregnated with aqueous solutions of $K_2CO_3$ to achieve a potassium loading level of 2 gm atom percent K per gm atom of combined metal, and then dried. For run 5, the powder was further impregnated with 1 gm atom percent Cu per gm atom of combined metal, and then dried.

Two grams of each spinel were loaded into the CSTR reactor with the results set forth in Table 2 below.

TABLE 2

PERFORMANCE OF K AND K—CU PROMOTED $Fe_{2.25}Mn_{0.75}O_4$ CATALYST

| Run | 1 | 2 | 3 | 4 | 5 |
|---|---|---|---|---|---|
| % K | — | 2.0 | 2.0 | 2.0 | 2.0 |
| % Cu | 1.0 | — | 1.0 | — | 1.0 |
| Surface Area ($M^2$/gm) | >50 | >50 | >50 | <5 | <5 |
| GMS Catalyst | 2.0 | 2.0 | 1.0 | 2.0 | 2.0 |
| % CO Conversion | 34 | 36 | 69 | Nil | Nil |
| Wt % Selectivity (based on $C_1$+ hydrocarbon basis) | | | | | |
| $CH_4$ | 8.8 | 3.5 | 1.7 | * | * |
| % α-olefin in $C_2$-$C_4$ | 78 | 91 | 94 | * | * |
| % α-olefin in $C_{10}$ | * | * | 63 | * | * |

Conditions: 270° C., 75 psi, 120:60:20 SCCM $H_2$:CO:$N_2$, 70-80 gms octacosane solvent, 20+ hr on stream.
*insufficient quantities of product generated for meaningful analysis.

The data in Table 2 show the superior slurry reactor behavior of the catalyst of this invention (Run 3) compared to both the relatively low surface area Fe-Mn catalysts (Run 4 and 5) and the high surface area spinel catalyst with only Cu (Run 1) or K (Run 2) promoters present. These data also show that with Cu and K promoters, the amount of CO conversion was nearly four times that obtained with the high surface area catalyst promoted with Cu or K only.

EXAMPLE 3

Effect of Fe:Mn Ratio

Four high surface area Cu and K promoted spinels were made following the procedure set forth in Example 1. One spinel had the composition set forth in Example 1 whereas the Fe:Mn ratio of the other two spinels was changed by varying the relative amounts of the ferric and manganese nitrate reagents. Two grams of each spinel were then loaded into the CSTR reactor, with the results listed in Tables 3 and 4 below.

TABLE 3

CSTR PERFORMANCE AS A FUNCTION OF Fe:Mn RATIO $Fe_{3-x}Mn_xO_4$/2% K, 1% Cu (>50 $M^2$/g spinels)

| X = | 0.75 | 1.5 | 2.75 |
|---|---|---|---|
| % CO Conversion | 83 | 30 | Nil |
| Wt % Selectivity (based on $C_1$+ hydrocarbons) | | | |
| $CH_4$ | 2.3 | 2.6 | NA |
| % α-olefin in $C_2$-$C_4$ | 93 | 86 | NA |

Conditions: 2.0 gms catalyst, 270° C., 75 psig, 120:60:20 SCCM $H_2$:CO:$N_2$, 72 gms octacosane solvent, 30+ hr on stream.

The data in Table 3 demonstrate the good activity and α-olefin selectivity obtained with the catalyst of the present invention containing Mn up to the Mn:Fe ratio of 1:3 i.e. x=0.75. In contrast, an identical catalyst containing higher levels of Mn where Mn:Fe=1:1 or 11:1, i.e. x=1.5 or 2.75, exhibited substantially lower activity under the indicated slurry reactor conditions.

TABLE 4

CSTR PERFORMANCE AS A FUNCTION OF Fe:Mn Ratio $Fe_{3-x}Mn_xO_4$/2% K, 1% Cu (>50 $M^2$/g spinels)

| X = | 0.15 | 0.75 |
|---|---|---|
| % CO Conversion | 79 | 87 |
| Wt % Selectivity (Based on $C_1$+ hydrocarbons) | | |
| $CH_4$ | 4.2 | 4.1 |
| % Olefin in $C_2$-$C_4$ | 94 | 92 |

Conditions: 8 gms catalyst, 270° C., 75 psig, 120:60:20 SCCM $H_2$:CO:$N_2$, 72 gms octacosane solvent, 30+ hr on stream.

The data in Table 4 demonstrate the high activity and α-olefin selectivity of the catalyst of the present invention when the Fe/Mn ratio is maintained in the range 3/1 to 19:1.

EXAMPLE 4

In this example, the CSTR performance of two high surface area glycolate derived spinels prepared according to the procedure set forth in Example 1 were compared to a potassium promoted, precipitated Fe-Mn oxide prepared according to the procedure of Kolbel in U.S. Pat. No. 4,177,203 and H. Schulz, Proceedings 8th Int. Congress on Catalysis, II, P. 123-133 (1985). Thus an aqueous solution of 57.5 g of $Mn(NO_3)_2.6H_2O$ in 100 cc of $H_2O$ was added to a solution of 7.23 g of $Fe(NO_3)_3.9H_2O$ dissolved in 10 cc of $H_2O$. The combined solutions were heated to 80° C. and about 100 cc of $NH_4OH$ was added to form a precipitate which was filtered and dried in air overnight at 110° C. Four g of the resulting powder was impregnated with 2 cc of a solution prepared by dissolving 0.85 g $K_2CO_3$ in 100 cc $H_2O$ and dried.

The results are set forth in Table 5.

TABLE 5

RELATIVE PERFORMANCE OF GLYCOLATE DERIVED SPINELS AND PRECIPITATED, LOW Fe—Mn RATIO CATALYSTS

|  | 2% K, 1% Cu Promoted Glycolate Derived Spinel | 0.5% K Promoted, Precipitated Fe—Mn |
|---|---|---|
| Fe:Mn | 3:1 1:11 | 1:11 |
| % CO Conversion | 83 Nil | Nil |
| Wt % Selectivity (based on $C_{1+}$ hydrocarbons) |  |  |
| $CH_4$ | 1.9 * | * |
| % α-olefin in $C_2-C_4$ | 93 * | * |

Conditions: 2 gms catalyst, 270° C., 75 psig, 120:60:20 SCCM $H_2$:CO:$N_2$, 72 gms octacosane, 20+ hr on stream.
*Insufficient quantities of product generated meaningful analysis.

The data in Table 5 demonstrate the superior performance of the catalyst of the present invention relative to a catalyst prepared by the method described in U.S. Pat. No. 4,177,203, etc. which was inactive in the slurry process. In addition, the catalyst prepared by the method of the present invention but containing Mn outside of the prescribed range, i.e. Fe:Mn=1:11 is found to be inactive under the low pressure slurry conditions employed.

EXAMPLE 5

In this example, the CSTR performance of a high surface area Cu and K promoted spinel of this invention was compared to a precipitated Fe-Mn oxide prepared according to the procedure set forth by Maiti et al. Thus, a catalyst was prepared by the procedure described by Maiti et al (Appl. Cat. 16(2), 215 (1985) in the Fe/Mn range where he observed his most olefinic products: 98.8 of $Fe(NO_3)_3.9H_2O$ and 2.2 gm $Mn(NO_3)_2.6H_2O$ were dissolved in 140 and 4 cc of $H_2O$ respectively and mixed to form a single solution. A 10 wt% $NH_4OH$ solution was added to bring the pH of the nitrate solution to 6.4. This solution was then heated to 70° C. This nitrate solution and the $NH_4OH$ solution were placed in two separatory funnels and while stirring constantly, each solution was added dropwise into a single mixing vessel maintaining the pH of the solution between 9.2 and 9.6 while the precipitate formed. The precipitate was filtered, and washed several times with $H_2O$, dried at 120° C. and finally calcined at 500° C.

The Maiti catalyst was charged into a CSTR reactor.

TABLE 6

RELATIVE PERFORMANCE OF GLYCOLATE DERIVED SPINELS AND PRECIPITATED, HIGH Fe/Mn RATIO CATALYSTS

|  | Glycolated Derived Spinel, K, Cu Promoted | Precipitated Prep. |
|---|---|---|
| Fe/Mn | 19:1 | 32 |
| WT catalyst (gm) | 1 | 2 |
| % CO conversion | 68.9 | 20.5 |
| $CH_4$ | 1.7 | 7.4 |
| % α-olefin, $C_2-C_4$ | 93.5 | 87.2 |

The results show the higher activity, olefinuity and lower methane selectivity with the catalyst of this invention vs. the preparation described in Appl. Cat. 16(2), 215 (1985).

EXAMPLE 6

In this Example, the CSTR performance of a high surface area Cu and K promoted spinel of this invention was compared to a precipitated and sintered Fe-Mn composition prepared according to the procedure set forth in U.S. Pat. No. 2,778,845.

An Fe/Mn catalyst was prepared as described by McGrath et al (U.S. Pat. No. 2,778,845). Thus, 10 gm of $Mn(NO_3)_2.6H_2O$ was dissolved in 2 cc of $H_2O$ by heating to 80° C. This was mixed with 54 gm of $Fe_3O_4$, the analog of Alan Wood magnetite. The paste which formed was dried overnight at 90° C. 0.35 gm of $K_2CO_3$ in 4 cc $H_2O$ was heated to 90° C. and mixed with the material dried above. An additional 2.5 cc of $H_2O$ was added to thoroughly mix the $K_2CO_3$ solution and the dried paste. This was then dried at 90° C. for several hours. This mix was heated to 1400° C. for 6 hours and cooled. The solidified chunk was ground and heated in a 20% $H_2$/80% He stream (at 500 cc/min total flow) at 371° C. for 48 hours. The catalyst was gently passivated at room temperature with a 1% $O_2$/99% He stream. 2 gms catalyst was loaded in 72 gm of octacocane. The results are shown in Table 7.

TABLE 7

RELATIVE PERFORMANCE OF GLYCOLATE DERIVED SPINELS AND HIGH TEMPERATURE Fe/Mn CATALYSTS

|  | Glycolated Derived Spinels Promoted With 2% K, 1% Cu | Precipitated Prep. |
|---|---|---|
| Fe:Mn | 3:1 | 7:1 |
| % CO conversion | 83 | Nil |
| Wt. % Selectivity (Based on $C_{1+}$ hydrocarbons) |  |  |
| $CH_4$ | 1.9 | * |
| % α-olefin, $C_2-C_4$ | 93 | * |

Conditions: 2 gms catalyst, 270°C., 75 psig, 120:60:20 SCCM $H_2$:CO:$N_2$, 72 gms octacosane, 20+ hr on stream.
*Insufficient quantities of product generated for meaningful analysis.

The data in Table 7 demonstrates the superior performance of the catalyst of the present invention relative to a catalyst prepared by the method described in U.S. Pat. No. 2,778,845, which was inactive in the slurry process.

What is claimed is:

1. A composition of matter comprising an unsupported, Group IA or IIA metal and copper promoted, single phase, iron-manganese spinel, said spinel exhibiting a powder X-ray diffraction pattern substantially isostructural with $Fe_3O_4$, and possessing a BET surface area greater than 30 $M^2$/g and an iron-manganese atomic ratio greater than about 2:1.

2. The composition of matter of claim 1 wherein said promotor metals are deposited substantially on the surface of said spinel.

3. The composition of matter of claim 2 wherein said surface area is at least about 50 $M^2$/g.

4. The composition of matter of any of claims 1, 2 or 3 wherein said spinel is of the formula: $Fe_xMn_yO_4$, wherein x and y are integer or decimal values, other than zero, and wherein the sum of x+y is 3, and the ratio of x/y is at least about 2:1.

5. The composition of matter of claim 4 wherein the ratio of x/y is in the range of from about 2:1–19:1.

6. The composition of matter of claim 5 wherein the ratio of x/y is about 3:1 to 7:1.

7. The composition of matter of claim 1 further comprising a mixture of said spinels in which at least two iron-manganese spinels are present, being isostructural with Fe₃O₄, each having BET surface areas greater than 30 M²/g, wherein said spinels individually possess different iron-manganese atomic ratios, which are at least 2:1.

8. The composition of matter of claim 1, 2 or 3 wherein said copper promoter is present in an amount of from about 0.1 to 10 gram-atom percent of metal ion based on the total gram-atoms of iron-manganese metals content.

9. The composition of matter of claim 2 wherein said copper promoter is present in an amount of from about 0.5 to 2 gram atom % of the iron-manganese metals content.

10. The composition of matter of claim 8 wherein said Group IA or IIA promoter metal is present in an amount of from about 0.1 to 10 gram-atom % of the total metals gram-atom of said composition.

11. The composition of any of claims 1, 2 or 7 wherein said composition is in its reduced-carbided form.

12. The composition of claim 4 wherein said composition is in its reduced-carbided form.

13. A process for producing a composition of matter comprising an unsupported, single phase, Group IA or IIA metal and copper promoted iron-manganese spinel, said spinel exhibiting a powder X-ray diffraction pattern substantially isostructural with Fe₃O₄, and possessing a BET surface area greater than 30 M²/g and an iron-manganese atomic ratio greater than about 2:1 comprising the steps of (a) evaporating a liquid solution comprising a mixture of iron and manganese salts of at least one alpha-hydroxy aliphatic carboxylic acid, wherein the molar ratio of total moles of said acid to total moles of said iron and manganese, taken as free metals, is about 1:1, or above, and wherein the atomic ratio of iron:manganese, taken as the free metals in said mixture, is greater than 2 to 1, yielding an amorphous residue; (b) calcining said residue at elevated temperature for a time sufficient to yield an iron-manganese spinel, exhibiting only one spinel phase, isostructural with Fe₃O₄, as determined by powder X-ray diffractometry; (c) impregnating the composition of (b) with a solution of a copper salt and a salt of a Group IA or IIA metal; and (d) drying the resulting impregnate.

14. The process of claim 13 wherein said acid is selected from glycolic, malic, tartaric, or lactic acids, or mixtures thereof.

15. The process of claim 14 wherein said solution is an aqueous solution.

16. A composition of matter comprising, a single phase, copper and Group IA or IIA metal promoted iron-manganese spinel produced by a process comprising the steps of (a) evaporating a liquid solution comprising a mixture of iron and manganese salts of at least one alpha-hydroxy aliphatic carboxylic acid, wherein the molar ratio of total moles of said acid to total moles of said iron and manganese, taken as free metals, is about 1:1, or above, and wherein the atomic ratio of iron:manganese, taken as the free metals in said mixture, is greater than 2 to 1, yielding an amorphous residue; (b) calcining said residue at elevated temperature for a time sufficient to yield a spinel; (c) impregnating the composition of (b) with a solution of a copper salt and a salt of a Group IA or IIA metal; and (d) drying the resulting impregnate.

* * * * *